(12) United States Patent
Bernard et al.

(10) Patent No.: US 11,351,062 B2
(45) Date of Patent: Jun. 7, 2022

(54) DEVICE AND METHOD FOR CUTTING A CORNEA OR CRYSTALLINE LENS

(71) Applicants: UNIVERSITE JEAN MONNET SAINT ETIENNE, Saint Etienne (FR); Centre National De La Recherche Scientifique, Paris (FR)

(72) Inventors: Aurelien Bernard, Saint Etienne (FR); Philippe Gain, Lyons (FR); Cyril Mauclair, Planfoy (FR); Gilles Thuret, Saint Just Saint Rambert (FR)

(73) Assignees: UNIVERSITE JEAN MONNET SAINT ETIENNE, Saint Etienne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 372 days.

(21) Appl. No.: 15/517,480

(22) PCT Filed: Oct. 7, 2015

(86) PCT No.: PCT/EP2015/073179
§ 371 (c)(1),
(2) Date: Apr. 6, 2017

(87) PCT Pub. No.: WO2016/055539
PCT Pub. Date: Apr. 14, 2016

(65) Prior Publication Data
US 2017/0304118 A1    Oct. 26, 2017

(30) Foreign Application Priority Data

Oct. 8, 2014 (FR) ...................... 1459624

(51) Int. Cl.
*A61F 9/00* (2006.01)
*A61F 9/008* (2006.01)
(Continued)

(52) U.S. Cl.
CPC .......... *A61F 9/00804* (2013.01); *A61F 9/009* (2013.01); *A61F 9/00825* (2013.01);
(Continued)

(58) Field of Classification Search
CPC ... A61F 9/00804; A61F 9/00817; A61F 9/008
See application file for complete search history.

(56) References Cited

U.S. PATENT DOCUMENTS 5,571,107 A * 11/1996 Shaibani ................. A61F 9/008
606/10
6,552,301 B2    4/2003 Herman et al.
(Continued)

FOREIGN PATENT DOCUMENTS

AU    2009346800 B2    4/2015
CA      2842474 A1    2/2013
(Continued)

OTHER PUBLICATIONS

Sinclair et al., "Interactive application in holographic optical tweezers of a multi-plane Gerchberg-Saxton algorithm for three-dimensional light Shaping", Optics Express, vol. 12, No. 8, Apr. 19, 2004, 6 pages.
(Continued)

*Primary Examiner* — Gary Jackson
*Assistant Examiner* — Anant A Gupta
(74) *Attorney, Agent, or Firm* — Womble Bond Dickinson (US) LLP

(57) ABSTRACT

A device for cutting human or animal tissue including a femtosecond laser that can emit a L.A.S.E.R. beam in the form of impulses. The device directs and focuses the beam onto or into the tissue for the cutting thereof. The device further includes and element to shape the L.A.S.E.R. beam, positioned in the trajectory of the beam, and to modulate the
(Continued)

energy distribution of the L.A.S.E.R. beam in the focal plane thereof, corresponding to the cutting plane.

10 Claims, 3 Drawing Sheets

(51) Int. Cl.
    *B23K 26/067*      (2006.01)
    *B23K 26/38*      (2014.01)
    *A61F 9/009*      (2006.01)
    *A61F 9/013*      (2006.01)
    *B23K 103/00*      (2006.01)

(52) U.S. Cl.
    CPC .......... *A61F 9/013* (2013.01); *B23K 26/0676* (2013.01); *B23K 26/38* (2013.01); *A61F 2009/0087* (2013.01); *A61F 2009/00872* (2013.01); *A61F 2009/00887* (2013.01); *A61F 2009/00889* (2013.01); *A61F 2009/00895* (2013.01); *B23K 2103/32* (2018.08)

(56) References Cited

U.S. PATENT DOCUMENTS

| | | | |
|---|---|---|---|
| 8,186,357 B2 * | 5/2012 | Lubatschowski | ....... A61F 9/008 128/898 |
| 8,262,647 B2 | 9/2012 | Raksi et al. | |
| 8,267,925 B2 | 9/2012 | Raksi et al. | |
| 8,506,559 B2 | 8/2013 | Raksi | |
| 8,585,686 B2 | 11/2013 | Bergt et al. | |
| 8,968,375 B2 | 3/2015 | Culbertson et al. | |
| 9,033,963 B2 | 5/2015 | Vera et al. | |
| 9,427,356 B2 | 8/2016 | Raksi | |
| 9,456,925 B2 | 10/2016 | Kurtz et al. | |
| 2003/0010763 A1 * | 1/2003 | Fukuchi | ............... B23K 26/064 219/121.73 |
| 2007/0121069 A1 * | 5/2007 | Andersen | ............ A61B 3/0008 351/221 |
| 2007/0193987 A1 * | 8/2007 | Bischoff | ............... G02F 1/3523 219/121.73 |
| 2010/0133246 A1 * | 6/2010 | Bor | .................... A61F 9/00829 219/121.72 |
| 2010/0270277 A1 * | 10/2010 | Matsumoto | ............ B23K 26/06 219/121.72 |
| 2011/0181929 A1 * | 7/2011 | Matsumoto | .......... B23K 26/032 359/15 |
| 2012/0271286 A1 | 10/2012 | Curatu et al. | |
| 2013/0114927 A1 | 5/2013 | Smith et al. | |
| 2013/0150837 A1 * | 6/2013 | Rathjen | ................... A61F 9/008 606/4 |
| 2014/0194862 A1 | 7/2014 | Smith et al. | |
| 2014/0200566 A1 | 7/2014 | Smith | |
| 2015/0094572 A1 | 4/2015 | Jang et al. | |
| 2015/0164689 A1 * | 6/2015 | Vogel | .................. A61F 9/00827 606/3 |
| 2015/0219937 A1 * | 8/2015 | Matsumoto | ........ B23K 26/0622 359/279 |
| 2015/0313760 A1 | 11/2015 | Telandro | |
| 2016/0067095 A1 | 3/2016 | Fu et al. | |
| 2016/0151202 A1 * | 6/2016 | Scarcelli | ................. A61F 9/008 606/5 |
| 2017/0157707 A1 * | 6/2017 | Landon | ................ B23K 26/046 |
| 2017/0304118 A1 | 10/2017 | Bernard et al. | |

FOREIGN PATENT DOCUMENTS

| | | | |
|---|---|---|---|
| CN | 102137731 A | 7/2011 | |
| DE | 102007019812 A1 | 10/2008 | |
| EP | 1279386 A1 | 1/2003 | |
| EP | 1790383 A1 | 5/2007 | |
| EP | 1834616 A1 | 9/2007 | |
| EP | 2335862 A1 | 6/2011 | |
| EP | 2434998 B1 | 5/2016 | |
| EP | 3203949 B1 | 3/2021 | |
| FR | 2957156 A1 | 9/2011 | |
| WO | 01/37769 A1 | 5/2001 | |
| WO | 02/94117 | 11/2002 | |
| WO | WO-02094117 A1 * | 11/2002 | ............. A61B 18/20 |
| WO | 2009/009246 A1 | 1/2009 | |
| WO | 2010024218 A1 | 3/2010 | |
| WO | 2011/071776 A1 | 6/2011 | |
| WO | 2016/055539 A1 | 4/2016 | |

OTHER PUBLICATIONS

International Search Report and Written Opinion received for PCT Patent Application No. PCT/EP2015/073179, dated Feb. 8, 2016, 20 pages (9 pages of English Translation and 11 pages of Original Document).
International Preliminary Report on Patentability received for PCT Patent Application No. PCT/EP2015/073179, dated Apr. 20, 2017, 15 pages (7 pages of English Translation and 8 pages of Original Document).
Office Action received for European Application No. 15788339.8, dated Jan. 21, 2019, 8 pages (4 pages of English Translation and 4 pages of Original Document).
Office Action received for European Application No. 15788339.8, dated May 3, 2018, 8 pages (4 pages of English Translation and 4 pages of Original Document).
Office Action received for European Patent Application No. 15788339.8, dated Dec. 5, 2019, 11 pages (6 pages of English Translation and 5 pages of Original Document).

* cited by examiner

DEVICE AND METHOD FOR CUTTING A CORNEA OR CRYSTALLINE LENS

TECHNICAL FIELD

The present invention relates to the technical field of surgical operations made with a femtosecond laser, and more particularly that of ophthalmologic surgery notably for applications for cutting-out corneas, or lenses.

The invention relates to a device and a method for cutting-out a human or animal tissue, such as a cornea, or a lens, by means of femtosecond laser.

The invention applies advantageously, but non-limiting, to cornea grafts cutout preserved in cornea banks, and to corneal cutout directly on the patient for corneal graft operations, such as vertical trepanations of different profiles, or parallel lamellar surface cutting.

By femtosecond laser, is meant a light source able to emit a L.A.S.E.R. beam as ultra-short pulses, for which the duration is comprised between 1 femtosecond and 100 picoseconds, preferably comprised between 1 and 1,000 femtoseconds, notably of the order of about hundred femtoseconds.

PRIOR ART

From the state of the art carrying out surgical operations of the eye is known by means of a femtosecond laser, such as operations for cutting-out corneas or lenses.

The femtosecond laser is therefore an instrument able of achieving dissection of the corneal tissue for example by focusing a L.A.S.E.R. beam in the stroma of the cornea, and by making a succession of small adjacent cavitation bubbles, which then forms a cutting-out line.

More specifically, during the focusing of the L.A.S.E.R. beam in the cornea, a plasma is generated by non-linear ionization when the intensity of the laser exceeds a threshold value, called an optical breakdown threshold. A cavitation bubble is then formed, generating a very localized perturbation of the surrounding tissues. Thus, the volume actually ablated by the laser is very small comparatively with the disrupted area.

The area cut out by the laser at each pulse is very small, of the order of one micron or of tens of microns depending on the power and the focusing of the beam. Thus, a corneal lamellar cutout may only be obtained by performing a series of contiguous impacts over the whole surface of the area to be cut out.

The displacement of the beam may then be carried out with a sweeping device, consisting of controllable galvanometric mirrors, and/or platens allowing the displacement of optical elements, such as mirrors or lenses. Another solution, reserved for cutting-out grafts, consists of moving not the L.A.S.E.R. beam but the graft itself by means of automated displacement platens.

These operations for displacement of the beam L.A.S.E.R. or of the graft itself are long and intricate. The surgical cutting-out operation is therefore slow and more difficult, given the extended time during which the patient may experience eye movements.

In fact, by way of example the average cutting-out time of a strip of 8 mm in diameter in a human cornea by a femtosecond laser of 5 kHz rate, with distinct impacts of 2 μm, is around forty minutes.

In order to optimize the cutting-out time, it is known how to increase the frequency of the laser. However, increasing the frequency also involves an increase in the displacement speed of the beam, by means of suitable platens or scanners. It is also known how to increase the spacing between the impacts of the laser on the tissue to be cutout, but generally to the detriment of the cutting-out quality.

Most femtosecond lasers for corneal cutout thus use high working frequencies, generally greater than 100 kHz, associated with systems for displacing the beam combining scanners and displacement platens, which are a burden to the total cost of the facility, and therefore of the invoiced surgical operation.

In order to remedy this rapidity problem of the L.A.S.E.R. cutting-out, it is also known how to use galvanometric mirrors for increasing the rate, the speed, and the deflection trajectory of the L.A.S.E.R. beam.

However, this technique does not give entire satisfaction in terms of results. The cutting-out speed may be further increased.

Another solution for reducing the cutting-out time consists of generating several cavitation bubbles simultaneously. Documents US 2010/0133246, EP 1 279 386 and DE 10 2007 019 812 describe cutting-out devices based on the subdivision technique of a single primary L.A.S.E.R. beam in a plurality of secondary L.A.S.E.R. beams. These devices generally comprise an optical system—such as one (or more) beam splitters—to produce secondary L.A.S.E.R. beams each generating a respective cavitation bubble.

The fact of simultaneously generating "n" cavitation bubbles gives the possibility of reducing the total duration for cutting-out a factor "n".

But, a major drawback to these devices is that it is very difficult to homogenise the energy contained in each of the secondary L.A.S.E.R. beams. In fact, it is necessary to modify elements of the optical system (for example modification of the position or of the orientation of a beam splitter, removal/replacement/addition of a lens, etc.) to "regulate" the optical system so as to generate uniform secondary L.A.S.E.R. beams. This avoids standardising the dimensions of the cavitation bubbles obtained from these secondary L.A.S.E.R. beams and controlling the position of the different cavitation bubbles relative to each other.

Also, the subdivision technique induces an increase in the diameter of the plurality of secondary L.A.S.E.R. beams relative to the diameter of the primary single L.A.S.E.R. beam produced by the femtosecond laser. In fact, the secondary L.A.S.E.R. beams correspond to « portions » of the spatially separated primary single L.A.S.E.R. beam. Due to the non-zero distance between the different secondary L.A.S.E.R. beams, the diameter of the circuit formed by the plurality of secondary L.A.S.E.R. beams is greater than the diameter of the primary L.A.S.E.R. beam.

This increase in diameter may be a drawback, notably in the event where the cutting-out device comprises a sweeping system—such as an optic scanner—for displacing the plurality of secondary L.A.S.E.R. beams in a cutting-out plane. In fact, the input diameter of a sweeping system is generally of the order of the diameter of the single primary L.A.S.E.R. beam such that some secondary beams fail to penetrate the sweeping system.

An object of the present invention is to propose a cutting-out device giving the possibility of finding a remedy to at least one of the aforementioned drawbacks.

DISCUSSION OF THE INVENTION

Therefore, the invention tends to propose a device and a method for cutting-out human or animal tissue, such as a cornea, or a lens, which perform rapid and viable cutting-out operations.

Another aim of the invention is to provide such a device and such a method which are of simple and inexpensive design.

To resolve the above problems, a cutting-out device has been developed comprising, as is known, a femtosecond laser able to emit a L.A.S.E.R. beam as pulses, and means able to direct and focus said beam on the tissue for its cutting-out as such.

According to the invention, the device further comprises shaping means for modulating the phase of the wave front of the L.A.S.E.R. beam, positioned on the trajectory of said beam, and control means for controlling the shaping means by applying an instruction determined to modulate the distribution of energy of the L.A.S.E.R. beam in at least two distinct impact points in its focal plane, corresponding to the cutting-out plane.

The control means comprise for example a computer or computers, a processor or processors, a microcontroller or microcontrollers, a micro-computer or micro-computers, a programmable automaton or automatons, a specific integrated application circuit or circuits, other programmable circuits, or other devices including a computer such as a workstation.

Within the scope of the present invention, by "impact point" is meant an area of the L.A.S.E.R. beam, comprised in its focal plane wherein the intensity of said L.A.S.E.R. beam is sufficient for generating a cavitation bubble in a tissue.

Thus, the invention gives the possibility of modifying the intensity profile of the L.A.S.E.R. beam in the cutting-out plane, so as to be able to improve the quality or else the speed of the cutting-out depending on the selected profile. This intensity profile modification is obtained by phase modulation of the L.A.S.E.R. beam.

The aim of the shaping is to modulate the final distribution of energy in the beam, for example to optimise a cutting-out laser.

The optical phase modulation is achieved by means of a phase mask. The energy of the incident L.A.S.E.R. beam is preserved after modulation, and the shaping of the beam is achieved by acting on its wave front. The phase of an electromagnetic wave represents the instantaneous situation of the amplitude of an electromagnetic wave. The phase depends both on the time and on the space. In the case of the spatial shaping of a L.A.S.E.R. beam, only the variation in the phase space are considered.

The wave front is defined as the surface of the points of a beam having an equivalent phase (i.e. the surface consisting of the points for which the travel times from the source having emitted the beam are equal). The modification of the spatial phase of a beam therefore requires modification of its wave front.

According to a particular embodiment of the invention, the shaping means are in the form of a spatial light modulator with liquid crystals.

Such a modulator, generally known under the abbreviation SLM, of the acronym "Spatial Light Modulator", comprises a layer of liquid crystals of controlled orientation for dynamically forming the wave front, and therefore the phase of the L.A.S.E.R. beam.

More precisely, an SLM is a light modulation device modulating the phase of an electromagnetic beam by means of liquid crystals. This system makes use of the anisotropy principle of liquid crystals, i.e., the modification of the index of the liquid crystals depending on their spatial orientation. Orientation of the liquid crystals may be achieved by means of an electric field. So locally modifying the liquid crystal index makes it possible to modify the wave front of the laser beam. This system may have a very strong resolution, compatible with complex shaping of beams.

The phase mask, i.e., the map illustrating how the phase of the beam must be modified to achieve distribution of given amplitude, is generally calculated by an iterative algorithm based on the Fourier transform, or on various optimisation algorithms such as genetic algorithms, or simulated annealing.

The SLM therefore dynamically forms the wave front of the L.A.S.E.R. beam since it is digitally configurable. This modulation enables shaping of the cutting-out beam dynamically and reconfigurably.

According to a particular embodiment, the energy of the L.A.S.E.R. beam is distributed so as to generate a plurality of L.A.S.E.R. impact points in a focusing plane of the L.A.S.E.R. beam.

Devices using an SLM (cf. US 2012/271286) have already been proposed. But in these devices the SLM is configured to correct aberrations of the electromagnetic beam stemming from the source of radiation (and not to distribute the energy of a L.A.S.E.R. beam in at least two distinct impact points in its focal plane by modulation of the phase of the wave front of said L.A.S.E.R. beam).

Within the scope of the present invention, from a Gaussian single beam shaping distributes its energy in several spots, limited in size and number by resolution of shaping means, and by the power of the beam. The number of spots diminishes as many times as necessary for the surgical cutting-out operation. In addition to a drop in cutting-out time, the present invention allows other improvements such as better surface quality after cutting-out or a drop in endothelial mortality. It is clear that the present invention may be combined with current techniques consisting of rapid displacement of the beam and at high cutting-out frequency to further boost cutting-out speed.

Therefore, reconfigurable modulation of the wave front of the femtosecond L.A.S.E.R. generates multiple simultaneous cutting-out points forming a pattern, each point of the pattern having a position controlled on a surface or in a volume of the cornea.

Within the scope of the present invention, by "pattern" is meant a plurality of L.A.S.E.R. impact points simultaneously generated in a focusing plane of a shaped L.A.S.E.R. beam—i.e. phase modulated for distributing its energy in several distinct spots in the focusing plane corresponding to the cutting-out plane of the device.

This technique gives the possibility of achieving the cutting-out operation in a more rapid and more efficient way since it applies several L.A.S.E.R. spots each achieving a cutout and according to a controlled profile.

The form of each point is preferably also modulable. This technique engages perfectly with existing techniques of scanners and/or displacement platens.

The different points of the pattern are preferably uniformly spaced over the two dimensions of the focal plane so as to form a grid pattern of L.A.S.E.R. spots In this way a single sweeping of the shaped L.A.S.E.R. beam to simultaneously generate a plurality of impact points replaces multiple sweepings of a « non-shaped » beam generating a single point of impact.

Another aim of the invention is to provide a method for cutting-out human or animal tissue, such as a cornea, or a lens, by means of a femtosecond laser able to emit a L.A.S.E.R. beam as pulses, focused on the tissue for its cutting-out as such.

According to the invention, and in keeping with the above, the method consists of:
- applying a phase modulation set value to shaping means of the L.A.S.E.R. beam, positioned on the trajectory of said beam,
- modulating the phase of the wave front of the L.A.S.E.R. beam with the shaping means, the modulation set value being calculated for distributing the energy of the L.A.S.E.R. beam in at least two impact points in its focal plane, corresponding to the cutting-out plane.

In this way, the method enables rapid and viable cutting.

SHORT DESCRIPTION OF THE DRAWINGS

Other features and advantages of the invention will become clearly apparent from the description which is made hereafter thereof, as an indication and by no means as a limitation, with reference to the appended figures, wherein.

DETAILED DISCUSSION OF THE INVENTION

The invention relates to a device for cutting-out (1) a human tissue by means of a femtosecond laser (2). In the subsequent description, the invention will be described, as an example, for cutting-out a cornea (3) of a human or animal eye.

Figure 1:
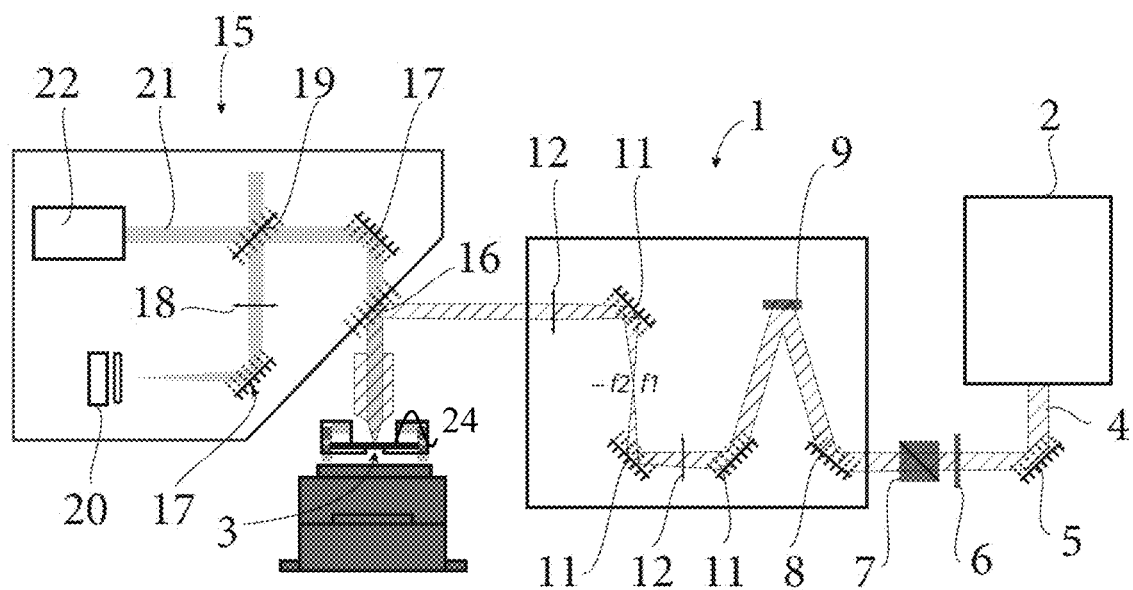
FIG. 1 is a schematic illustration of a circuit of the cutting-out device according to the invention.

In reference to FIG. 1 illustrating the circuit of such a cutting-out device (1), the latter comprises a femtosecond laser (2) able to emit a L.A.S.E.R. beam as pulses. As an example, the laser emits a light with a wavelength of 780 nm as pulses of 150 femtoseconds. The laser has a power of 2 W and a frequency of 5 kHz.

The L.A.S.E.R. beam (4) emitted by the laser (2) is directed and focused onto the cornea to be cut out by means of a plurality of optical elements. More precisely, a first mirror (5) reflects the L.A.S.E.R. beam (4) stemming directly from the laser (2), and sends it back to a half-wave plate (6) well known from the prior art to produce phase shift by 180°, i.e., a delay by half a wavelength. The outgoing wave of such a plate (6) presents symmetric polarization of the incoming wave relative to optical axis.

The L.A.S.E.R. beam (4) stemming from the half-wave plate (6) then passes through a polarizing cube (7) also known from the prior art, for separating random polarization of the L.A.S.E.R. beam (4) into two orthogonal and linear polarization components. One of the components is reflected at 90°, while the other component is transmitted. The transmitted polarization component is then reflected onto a second mirror (8) as far as shaping means (9) of the L.A.S.E.R. beam (4).

The spatial shaping means of the L.A.S.E.R. beam (4) in the focal plane give the possibility of varying the wave surface of the L.A.S.E.R. beam (4) in order to obtain impact points separated from each other in the focal plane.

More specifically, the shaping means allow modulation of the phase of the L.A.S.E.R. beam (4) stemming from the femtosecond laser in order to form intensity peaks in the focal plane of the beam, each intensity peak producing a respective impact point in the focal plane corresponding to the cutting-out plane.

The shaping means are, according to the illustrated embodiment, a spatial light modulator with liquid crystals, known under the acronym of SLM, for "Spatial Light Modulator".

The SLM (9) allows modulation of the final distribution of energy of the L.A.S.E.R. beam (4), notably in the focal plane corresponding to the cutting-out plane of the cornea.

More specifically, the SLM is adapted for modifying the spatial profile of the wave front of the primary L.A.S.E.R. beam (4) stemming from the femtosecond laser (4) for distributing the energy of the L.A.S.E.R. beam (4) in different focusing spots in the focusing plane.

The SLM (9) is a device well known from the prior art and comprises a layer of liquid crystals with controlled orientation for dynamically forming the wave front, and therefore the phase of the L.A.S.E.R. beam (4). The layer of liquid crystals of an SLM is organized like a grid (or matrix) of pixels. The optical thickness of each pixel is electrically controlled by orienting the liquid crystal molecules belonging to the surface corresponding to the pixel.

The SLM (9) makes use of the anisotropy principle of liquid crystals, i.e. the modification of the index of the liquid crystals, depending on their spatial orientation. The orientation of liquid crystals may be achieved by means of an electric field. Thus, the modification of the index of the liquid crystals modifies the wave front of the L.A.S.E.R. beam (4).

In a known way, the SLM (9) applies a phase mask (10), i.e. a map determining how the phase of the beam (4) has to be modified for obtaining a given amplitude distribution in its focusing plane.

The phase mask is a two-dimensional image, each point of which is associated with a respective pixel of the SLM. This phase mask gives the possibility of controlling the index of each liquid crystal of the SLM by converting the value associated with each point of the mask—illustrated in gray levels comprised between 0 and 255 (therefore from black to white)—into a control value—represented in a phase comprised between 0 and $2\pi$. Thus, the phase mask is a modulation set value displayed on the SLM for causing by reflection an uneven spatial phase shift of the L.A.S.E.R. beam (4) illuminating the SLM. Of course, one skilled in the art will appreciate that the gray level range may vary depending on the SLM version used. For example in certain cases, the gray level range may be comprised between 0 and 220.

The phase mask (10) is generally calculated by an iterative algorithm based on the Fourier transform, or on diverse optimization algorithms, such as genetic algorithms, or simulated annealing. Different phase masks may be applied to SLMs depending on the number and on the position of the impact points desired in the focal plane of the L.A.S.E.R. beam (4). In every case, one skilled in the art knows how to calculate a value in each point of the phase mask in order to distribute the energy of the L.A.S.E.R. beam (4) in different focusing spots in the focal plane.

The SLM (9) therefore dynamically forms the wave front of the L.A.S.E.R. beam (4). This modulation enables shaping of the cutting-out beam (4) dynamically and reconfigurably.

Figure 3:
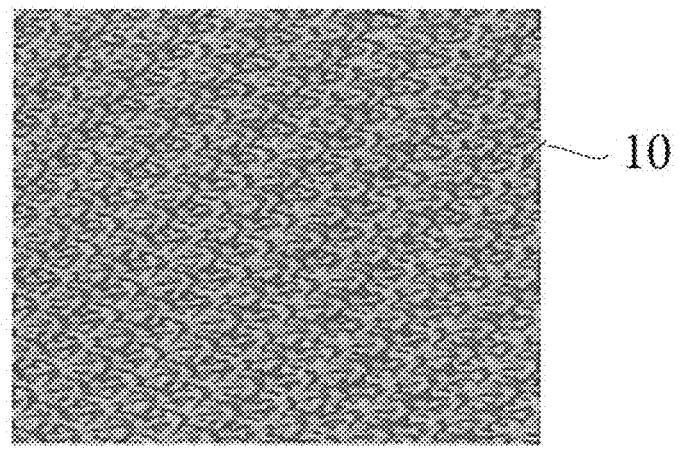
FIG. 3 is a representation illustrating a phase mask for obtaining distribution of energy such as in FIG. 2.

The SLM (9) gives the possibility, from a Gaussian L.A.S.E.R. beam (4) generating a single impact point, and by means of the phase mask, (10) such as shown in FIG. 3, of distributing its energy by phase modulation so as to simultaneously generate several impact points in its focusing plane.

The invention therefore proposes generating a plurality of impact points from a single L.A.S.E.R. beam shaped by phase modulation (a single beam upstream and downstream of the SLM), by contrast to the devices of US 2010/0133246, EP 1 279 386 and DE 10 2007 019 812 in which the plurality of L.A.S.E.R. impact points is obtained by subdivision of a primary beam in a plurality of secondary beams (a single beam upstream of a beam splitter and several beams downstream of the splitter), each secondary beam generating a respective impact point.

The L.A.S.E.R. beam (4) formed by phase modulation is then directed towards a succession of mirrors (11) and optic lenses (12), arranged for directing and focusing said beam formed by phase modulation (4) on the surface of the cornea (3) to be cutout. A plurality of L.A.S.E.R. spots (13) is focused in the cornea (3), each spot (13) being able of achieving a cutting-out operation of the cornea (3).

Figure 2:
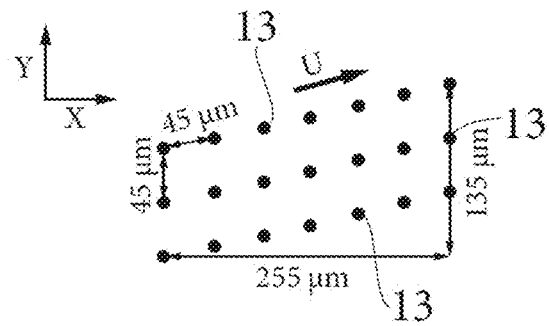
FIG. 2 is a schematic representation of possible shaping of the L.A.S.E.R. beam of the cutting-out device according to the invention.

In reference to FIG. 2, the different L.A.S.E.R. spots (13) obtained are, for example, uniformly spaced over two dimensions of the focal plane of the L.A.S.E.R. beam (4) so as to form a grid pattern of L.A.S.E.R. spots (13). By way of example, shaping of the L.A.S.E.R. beam (4) by phase modulation obtained with the phase mask (10) may enable formation of a pattern composed of three lines of 7 spots (13), spaced from each other by 45 µm according to the two dimensions of said focal plane corresponding to the cutting-out plane.

The number of spots of the pattern diminishes as many times as necessary for the surgical cutting-out operation. In addition to the cutting-out time of the cornea (3), the present invention enables other improvements, such as better surface quality after cutting-out or a drop in endothelial mortality. It is clear that the present invention may be combined with current techniques consisting of rapid displacement of the beam or beams (4), and at high cutting-out frequency to further boost the cutting-out speed.

The reconfigurable modulation of the wave front of the femtosecond L.A.S.E.R. generates multiple simultaneous cutting-out points each having a controlled position on a surface or in a volume of the cornea (3).

It emerges from the above that the invention therefore performs a surgical cutting-out operation of a cornea, rapidly and efficiently as it carries out several L.A.S.E.R. spots (13) each carrying out cutting-out and according to a controlled profile.

The SLM (9) may also be configured to form the wave front of the L.A.S.E.R. beam (4) in any other way. For example, the L.A.S.E.R. spot obtained for executing cutting-out of the cornea may have any geometric form, other than circular. This may have certain advantages depending on the considered application, such as an increase in the speed and/or the quality of the cutout.

Figure 4:
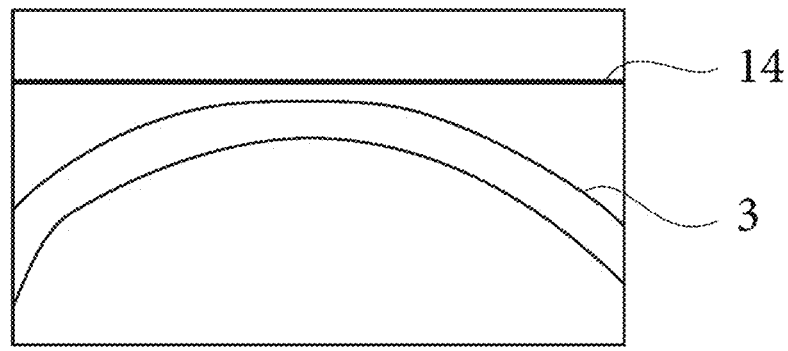
FIG. 4 is a representation illustrating a corneal graft prior to the cutting-out operation.
Figure 5:
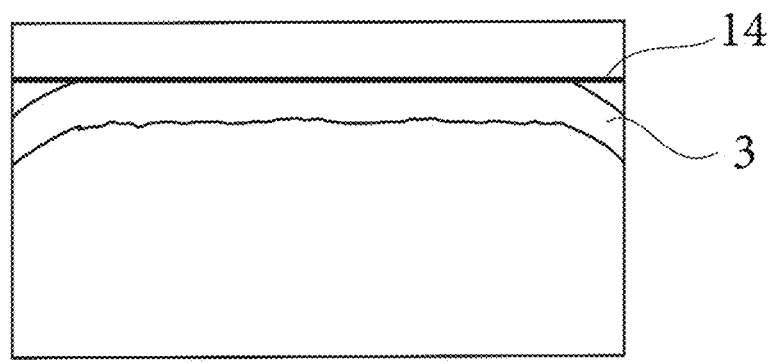
FIG. 5 is a representation similar to that of FIG. 4, the corneal graft being shown after having been leveled.
Figure 6:
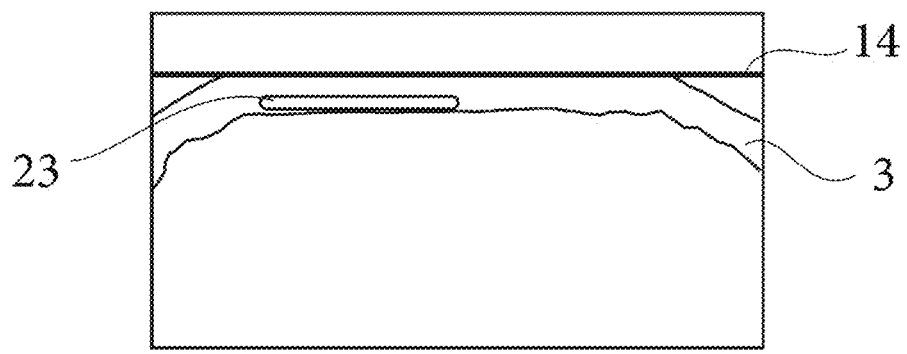
FIG. 6 is a representation similar to that of FIG. 5, illustrating the corneal graft after initial cutting-out laser is completed.

Advantageously, and in reference to FIGS. 4 and 5, the surface of the cornea (3) to be cut out is leveled by means of a levelling strip (14) well known from the prior art. This strip (14) allows levelling of the corneal curvature, simplifying the cutting-out trajectory of the L.A.S.E.R. spots (13) and improving the cutting-out speed. The strip (14) also serves as reference for positioning according to an axis Z of the L.A.S.E.R. spots (13), i.e., according to an axis orthogonal to the cutting-out plane. In this way, the levelling strip (14) enables better cutting-out precision of grafts. Each spot (13) makes an impact in the cornea, vaporizing the tissue of said cornea so as to form a cutting-out point (23).

Finally, to enable precise positioning of the cornea (3) to be cutout, the circuit comprises confocal display set-up (15). This circuit (15) produces positioning precision close to a micrometer of the cornea according to the axis Z. In reference to FIG. 1, this circuit (15) comprises a dichroic mirror (16) and a focusing lens (24) able of reflecting, directing and focusing some of the intensity of the beam (4) formed by phase modulation, specifically of the beam (4) stemming from the SLM (9), towards the surface of the cornea (3) to be cutout. The other part of the intensity of the beam (4) formed is directed to an array comprising mirrors (17), a lens (18), and a second dichroic mirror (19), arranged both to direct some of the intensity of the beam (4) stemming from the dichroic mirror (16) towards a CCD sensor (20) and, on the other hand, to direct a second L.A.S.E.R. beam (21), stemming from a second light source (22) towards the dichroic mirror (16) and the surface of the cornea (3) to be cutout. This circuit (15) does not form part of the invention and will not be described in more detail.

The invention proposes an original method based on phase modulation of the wave front of a L.A.S.E.R. beam for redistributing the energy of said L.A.S.E.R. beam in a plurality of distinct impact points of said L.A.S.E.R. beam. Several impact points are generated from a single modulated L.A.S.E.R. beam.

This phenomenon may be seen as a two-dimensional interference phenomenon. Each portion of the initial L.A.S.E.R. beam stemming from the source is delayed or advanced relatively to the initial wave front so that each of these portions are redirected so as to produce constructive interference in N distinct points in the focal plane of a lens. This energy redistribution in a plurality of impact points only occurs in a single plane (i.e. the focusing plane) and not at all along the propagation path of the modulated L.A.S.E.R. beam. Thus, the observation of the modulated L.A.S.E.R. beam before or after the focusing plane does not give the possibility of identifying a redistribution of the energy in a plurality of distinct impact points, because of this phenomenon which may be assimilated to constructive interferences (which only take place in a plane and not at all along the propagation like in the case of the separation of an initial L.A.S.E.R. beam in a plurality of secondary L.A.S.E.R. beams).

Figure 7:
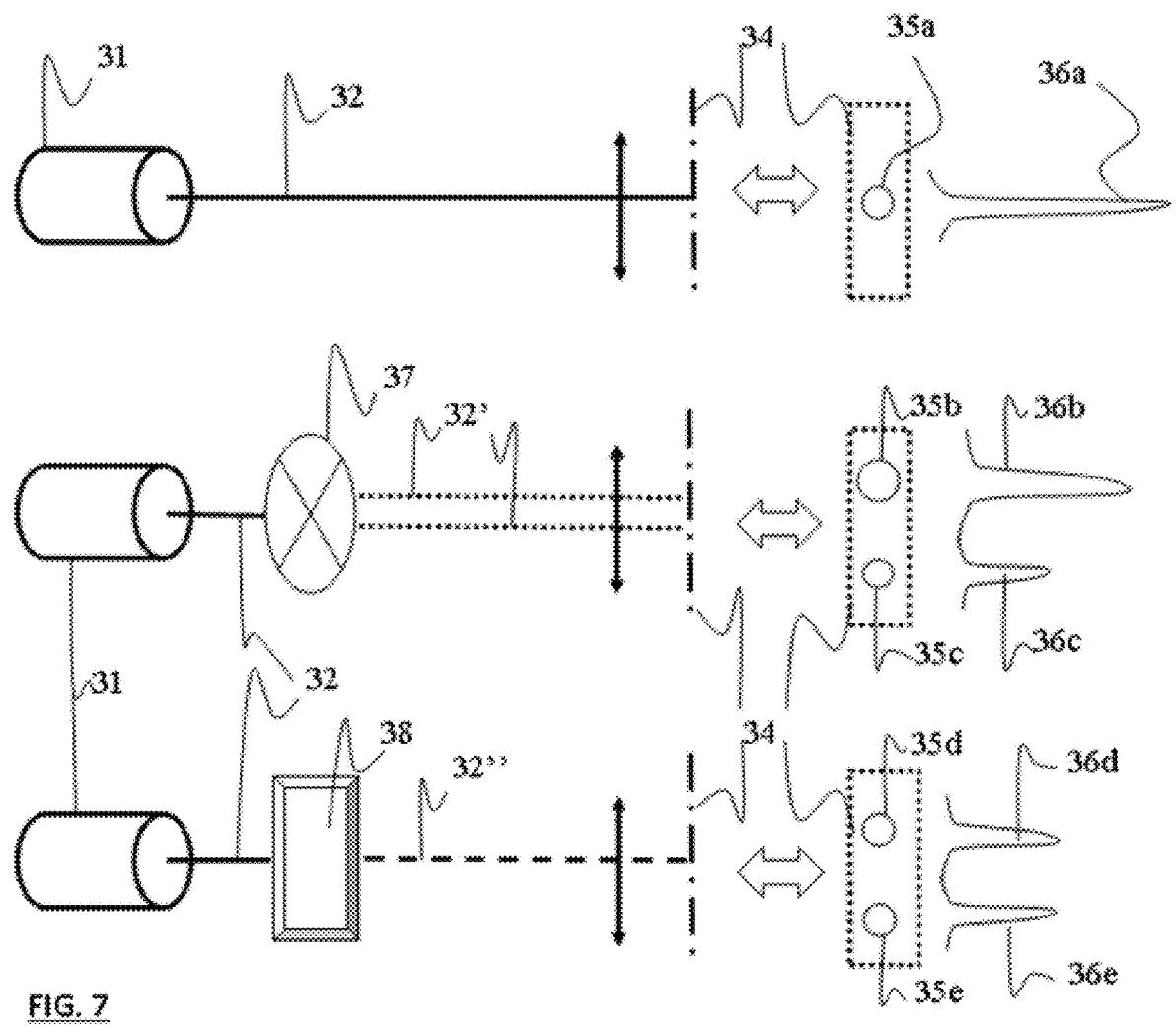
FIG. 7 illustrates an intensity distribution of a L.A.S.E.R. beam in its focal plane.

In order to better understand this phase modulation phenomenon of the wave front, FIG. 7 schematically illustrates profiles of intensity profiles 36a-36e obtained for three examples of distinct optical circuits have been schematically illustrated in FIG. 7.

As illustrated in FIG. 7, a L.A.S.E.R. beam 32 emitted by a laser source 31 produces an intensity peak 36a with a Gaussian shape in an impact point 35a in a focusing plane 34.

The insertion of a beam splitter 37 between the source 31 and the focusing plane 34 induces the generation of a plurality of secondary L.A.S.E.R. beams 32', each secondary L.A.S.E.R. beam 32' producing a respective impact point 35b, 35c in the focusing plane 34 of the secondary L.A.S.E.R. beams 32'.

Finally, the insertion between the source 31 and the focusing plane 34 of an SLM 38 programmed by means of a phase mask forming a modulation set value induces modulation of the phase of the wave front of the L.A.S.E.R. beam 32 stemming from the source 31. The L.A.S.E.R. beam 32" for which the phase of the wave front has been modulated gives the possibility of inducing production of several intensity peaks 36d, 36e spatially separated in the focal plane 34 of the L.A.S.E.R. beam, each peak 36d, 36e corresponding to a respective impact point 35d, 35e producing a cutout.

The original method according to the invention based on a modulation of the phase of the wave front gives the possibility of generating several simultaneous cavitation bubbles without any multiplication of the initial L.A.S.E.R. beam produced by the femtosecond L.A.S.E.R. source, in contrast to systems and methods proposes in the prior art which utilise optical beam duplication devices such as beam splitters (cf. US 2010/0133246, EP 1 279 386 and DE 10 2007 019 812).

To better understand this modulation phenomenon, an example is a wave spreading through an optical system which will be absorbed into a thin lens of focus f. The object $\vec{E}(\vec{r},z)$ and image $\vec{E}(\vec{r}',z')$ electrical fields located respectively in the object and image focal planes of a lens are linked by the following relationship: $\vec{E}(\vec{r}',z') \sim TF(\vec{E}(\vec{r},z))$. On the other hand, the electric field of an electromagnetic wave solution of the propagation equation may be expressed in the form: $E(\vec{r},z)=|E(\vec{r},z)|e^{i\varphi(\vec{r},z)}$, where $\varphi(\vec{r},z)$ is called spatial phase. Experimentally, it is noted that the influence of the spatial phase in the object field has a major influence on the distribution of amplitude in the image plane. By way of careful choice of the spatial phase in the object field it is possible to obtain arbitrary distribution of the amplitude in the field image (in the present case, in the focal point of the lens). The same considerations apply when the object and image fields do not coincide with the focal planes. Consideration must be given to propagation of the wave in the phase calculation (calculation not detailed here).

Digital addressing of the SLM makes for easier programming. It is possible to finely adjust the SLM to produce uniform impact points 35d, 35e in the focusing plane 34, not possible with the beam separation technique for which resulting dimensions and positions of the impact points 35b, 35c may be very heterogeneous and for which in this case it is not possible to correct these defects dynamically, the separation techniques of the beam being based on rigid optical elements.

Fine adjustment of the SLM is achieved by varying the phase mask used to control it.

The SLM may be adjusted by placing a beam analyser (such as a CCD camera) in the focusing plane and projecting the modulated L.A.S.E.R. beam onto the beam analyser. The values of the phase mask are then varied to where intensity peaks of uniformly distributed uniform dimensions are obtained. Once the phase mask is calculated precisely, it may be utilised in all manufactured cutting-out devices. It is recorded as a modulation set value in the memories of control means of devices to control their respective SLM by means of said phase mask. So once it is calculated, the phase mask is fixed and is not modified depending on the properties (i.e. form of the wave front) of the L.A.S.E.R. beam to which SLM is linked.

In this sense, the phase mask is calculated independently of the form of the wave front of the L.A.S.E.R. beam prior to modulation, contrary to the phase mask of SLM used to correct aberrations as proposed in the prior art.

Figure 8:
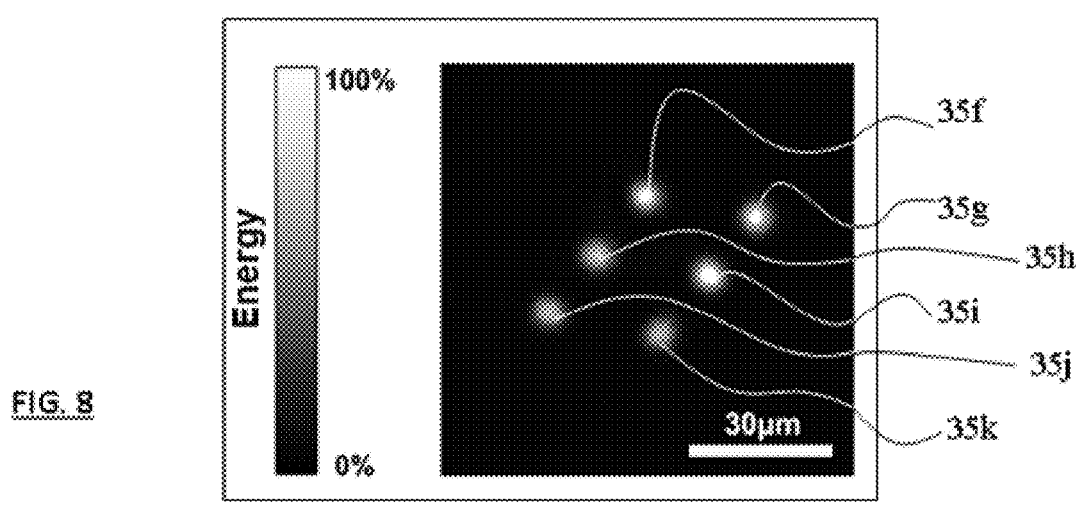
FIG. 8 illustrates the intensity distribution obtained by modulating the phase of the front of a L.A.S.E.R. beam by way of a spatial light modulator

By way of example, phase modulation has experimentally produced a matrix of laser spots 35f-35k of such uniformity that each spot 35f, 35g, 35h, 35i, 35j, 35k has the same fluence ridge at less than around 5%, a measurement taken by means of a CCD sensor, as illustrated in FIG. 8.

Simultaneous generation of several impact points by beam duplication also does not easily and precisely control the position and the dimensions in cross-section of the different secondary beams.

Thus, the invention gives the possibility of having an efficient cutting-out tool, since the L.A.S.E.R. impacts are obtained with substantially equal energy spots, the cavitation bubbles which pull to pieces the cutout biological tissues will be of substantially equal sizes. This gives the possibility of improving the quality of the obtained result, with a homogeneous cutting-out plane, in which the residual tissue bridges all has substantially the same size and which allows dissection by the practitioner of acceptable quality considering the importance of the quality of the surface condition of the cutout tissue when for example this is a cornea. The systems and methods proposed in the prior art which utilise optical beam duplication devices such as beam splitters (cf. US 2010/0133246, EP 1 279 386 and DE 10 2007 019 812) do not produce a uniform cutting-out plane due to the impossibility of precisely controlling the placement of each beam and distribution of the energy in each beam, resulting in non-uniform tissue cutting-out with tissue bridges of different size, and dissection which is sometimes easy, sometimes difficult, and which fails to ensure an acceptable surface condition of the cut out tissue.

Also, having a number of identical impact points, the diameter in cross-section of a plurality of beams duplicated is greater than the diameter in cross-section of a phase-modulated L.A.S.E.R. beam according to the invention. This is due to the fact that the duplicated beams must be spaced by a sufficient distance to limit risk of interferences.

So to generate a plurality of impact points, it will be easier to link a phase-modulated L.A.S.E.R. beam according to the invention to an optical element having an input of limited dimensions rather than a plurality of secondary L.A.S.E.R. beams.

For example, the phase-modulated L.A.S.E.R. beam according to the invention is compatible with use of an optical sweeping scanner composed of one (or more) optical mirrors pivoting about at least two axes.

Integration of such an optic scanner in the cutting-out device according to the invention displaces the pattern of impact points (formed by the phase-modulated L.A.S.E.R. beam to distribute the energy of the L.A.S.E.R. beam in at least two distinct impact points) in the cutting-out plane in a plurality of distinct positions. Such a displacement system may be controlled by the control means of the cutting-out device.

The invention was described for operations for cutting-out a cornea (3) in the field of opthalmological surgery, but it is obvious that it may be used for another type of operation in opthalmological surgery without departing from the scope of the invention. For example, the invention finds application in corneal refractive surgery, such as the treatment of ametropias, notably nearsightedness, farsightedness, astigmatism, in the treatment of loss of accommodation, notably farsightedness.

The invention also finds application in the treatment of cataract with incision of the cornea (3), cutting-out of the anterior lens capsule, and fragmentation of the lens. Finally, in a more general way, the invention relates to all clinical or experimental applications in the cornea (3) or the lens of a human or animal eye.

Still more generally, the invention relates to the vast field of L.A.S.E.R. surgery, and finds an advantageous application when the purpose is to cutout and more particularly vaporize human or animal soft tissues, with a high water content.

The invention claimed is:

1. A medical device configured to cut a human or animal tissue, said device comprising:
   a femtosecond laser which emits a L.A.S.E.R. beam as pulses,
   shaping means of the L.A.S.E.R. beam, said shaping means being positioned on the trajectory of said L.A.S.E.R. beam, wherein said shaping means includes a spatial light modulator which displays a phase modulation set value which causes the generating of a single modulated L.A.S.E.R. beam by modulating the phase of the wave front of the L.A.S.E.R. beam emitted by the femtosecond laser,
   control means configured to apply the phase modulation set value to the shaping means, said phase modulation set value being calculated by the control means for distributing the energy of the single modulated L.A.S.E.R. beam in at least two impact points in a focal plane of said single modulated L.A.S.E.R. beam, each impact point generating a cavitation bubble within the human or animal tissue, wherein resulting residual tissue bridges are all substantially the same size,
   means configured to direct and focus said single modulated L.A.S.E.R. beam in the human or animal tissue in order to cut said human or animal tissue, and
   an optical sweeping scanner configured to displace the at least two impact points in a plurality of distinct positions in the focal plane of said single modulated L.A.S.E.R. beam.

2. The medical device according to claim 1, wherein the spatial light modulator is in the form of a spatial light modulator with liquid crystals.

3. The medical device according to claim 1, wherein the phase modulation set value is a two-dimensional image displayed on the spatial light modulator, wherein said two-dimensional image causes an uneven spatial phase shift of the L.A.S.E.R. beam by reflection, said uneven spatial phase shift inducing distribution of energy of the single modulated L.A.S.E.R. beam in at least two impact points in the focal plane of said single modulated L.A.S.E.R. beam.

4. The medical device according to claim 1, wherein the phase modulation set value is a two-dimensional grey level image calculated by an iterative algorithm based on a Fourier transform.

5. The medical device according to claim 1, wherein the phase modulation set value is calculated independently of the form of the wave front of the L.A.S.E.R. beam prior to modulation.

6. The medical device according to claim 1, wherein the energy of the single modulated L.A.S.E.R. beam is distributed in the focal plane in a plurality of distinct L.A.S.E.R. impact points forming a pattern, each point generating a cavitation bubble in the human or animal tissue.

7. The medical device according to claim 6, wherein the L.A.S.E.R. impact points of the pattern are uniformly spaced over the two dimensions of the focal plane so as to form a grid pattern of L.A.S.E.R. spots.

8. The medical device according to claim 6, wherein the optical sweeping scanner comprises an optical mirror system pivoting about at least two axes for displacing the pattern in a plurality of distinct positions in the focal plane of said single modulated L.A.S.E.R. beam.

9. A method of controlling a medical device configured to cut a human or animal tissue, said device comprising a femtosecond laser which emits a L.A.S.E.R. beam as pulses, shaping means of the L.A.S.E.R. beam, the shaping means including a spatial light modulator configured to generate a single modulated L.A.S.E.R. beam by modulating the phase of the wave front of the L.A.S.E.R. beam emitted by the femtosecond laser,
   control means for controlling the shaping means, and
   means for directing and focusing the single modulated L.A.S.E.R. beam in the human or animal tissue,
   an optical sweeping scanner configured to displace the single modulated L.A.S.E.R. beam
   wherein the method comprises the steps of:
      Calculating by the control means, of a phase modulation set value for distributing the energy of the single modulated L.A.S.E.R. beam in at least two impact points in a focal plane of said single modulated L.A.S.E.R. beam, each impact point generating a cavitation bubble in the human or animal tissue, wherein resulting residual tissue bridges are all substantially the same size,
      applying by the control means, of the phase modulation set value to the shaping means, said shaping means being positioned on the trajectory of said L.A.S.E.R. beam,
      displaying by the spatial light modulator, of the phase modulation set value, for causing the generating of said single modulated L.A.S.E.R. beam by modulating the phase of the wave front of the L.A.S.E.R. beam emitted by the femtosecond laser,
      focusing by the means for directing and focusing, of the single modulated L.A.S.E.R. beam in the human or animal tissue,
      Displacing by the optical sweeping scanner of the at least two impact points in a plurality of distinct positions in the focal plane of said single modulated L.A.S.E.R. beam.

10. The method of claim 9, wherein the step of calculating comprises the substep of using an iterative algorithm based on a Fourier transform to determine a two-dimensional grey level image constituting the phase modulation set value.

* * * * *